US007037540B2

(12) United States Patent
Elder et al.

(10) Patent No.: US 7,037,540 B2
(45) Date of Patent: *May 2, 2006

(54) METHOD FOR REDUCING ACRYLAMIDE FORMATION IN THERMALLY PROCESSED FOODS

(75) Inventors: Vincent Allen Elder, Carrollton, TX (US); John Gregory Fulcher, Dallas, TX (US); Henry Kin-Hang Leung, Plano, TX (US)

(73) Assignee: Frito-Lay North America, Inc., Plano, TX (US)

( * ) Notice: Subject to any disclaimer, the term of this patent is extended or adjusted under 35 U.S.C. 154(b) by 355 days.

This patent is subject to a terminal disclaimer.

(21) Appl. No.: 10/247,504

(22) Filed: Sep. 19, 2002

(65) Prior Publication Data

US 2004/0058054 A1   Mar. 25, 2004

(51) Int. Cl.
  *A23B 7/155*   (2006.01)
  *A23J 3/34*   (2006.01)
  *A23L 1/217*   (2006.01)
  *A23L 3/3571*   (2006.01)

(52) U.S. Cl. .......................... 426/52; 426/20; 426/549; 426/44; 426/637

(58) Field of Classification Search ................ 426/18, 426/19, 20, 21, 23, 27, 55, 56, 60, 49, 52, 426/69, 549, 626, 618, 44, 653, 656, 637, 426/438, 465
See application file for complete search history.

(56) References Cited

U.S. PATENT DOCUMENTS

| 3,620,925 A | * | 11/1971 | Kazuo et al. | ............... 435/229 |
| 3,652,402 A | * | 3/1972 | Chibata et al. | ............. 435/229 |
| 3,773,624 A | * | 11/1973 | Wagner et al. | .............. 435/229 |
| 3,914,436 A | * | 10/1975 | Nakadai et al. | ............... 426/46 |
| 4,272,554 A | | 6/1981 | Schroeder et al. | |
| 5,514,387 A | * | 5/1996 | Zimmerman et al. | ......... 426/74 |

OTHER PUBLICATIONS

Mottram et al., "Acrylamide is formed in the Maillard reaction", Nature, vol. 419, p. 448: Oct. 3, 2002.*
Kim et al., "Asparaginase II of *Saccharomyces cerevisiae*", The Journal of Biological Chemistry, 263(24): 11948-11953; Aug. 25, 1988.*

U.S. Department of Health & Human Services article entitled "Exploratory Data on Acrylamide in Foods", found at http://www.mindfully.org/Food/Acrylamide-Foods-FDA, Dec. 4, 2002 (9 pgs).
Don Mottram—The University of Reading, "Acrylamide in Cooked Foods—the Latest "Food Scare"", 2002 (44 pgs.).
Report from Swedish Scientific Expert Committee of the Swedish National Food Administration, "Acrylamide in Food—Mechanisms of Formation and Influencing Factors During Heating of Foods", Apr. 24, 2002 (22 pgs.).
Amanda Yarnell, Chemical & Engineering News article entitled "Acrylamide Mystery Solved", found at http://pubs.acs.org/cen/today/oct4.html, Oct. 4, 2002 (3 pgs.).
Janet Raloff, Science News Online article entitled "Hot Spuds: Golden Path to Acrylamide in Food", found at http://www.sciencenews.org/20021005/fob5.asp, Week of Oct. 5, 2002, vol. 162 (3 pgs.).
Lauran Neergaard, Health Zone article entitled "Scientists: Chemical Reaction May Create Carcinogen", found at http://www.cjonline.com/stories/093002/hea_carcinogen.shtml, Sep. 30, 2002 (3 pgs.).
Procter & Gamble article entitled "New Findings Show Acrylamides Are Found in a Wider Variety of Foods and May Lead to New Ways of Reducing Acrylamide Levels" found at http://biz.yahoo.com/prnews/020927/clf005_1.html, Sep. 27, 2002 (2 pgs.).
Center for Science in the Public Interest article entitled "New Tests Confirm Acrylamide in American Foods", found at http://www.cspinet.org/new/20020625.html, Jun. 25, 2002 (2 pgs.).
World Health Organization Deptartment of Food Safety Report "FAO/WHO Consultation on the Health Implications of Acrylamide in Food", Joint FAO/WHO Consulation, Geneva, Jun. 25-27, 2002 found at http://www.who.int/fsf/Acrylamide/SummaryreportFinal.pdf (8 pgs.).

(Continued)

*Primary Examiner*—Keith Hendricks
(74) *Attorney, Agent, or Firm*—Colin P. Cahoon; Carstens & Cahoon, LLP

(57) ABSTRACT

A process and apparatus for a method for reducing the amount of acrylamide in thermally processed foods. This invention permits the production of foods having significantly reduced levels of acrylamide. The method relies on interfering with an acrylamide formation pathway that begins with the amino acid asparagine.

13 Claims, No Drawings

OTHER PUBLICATIONS

U.S. Department of Health and Human Services, Public Health Service, National Toxicology Program, 9th Report on Carcinogens Revised Jan. 2001 found at http://win2000.kreatiweb.it/sanitaweb/web/Biblioteca/carcinogens/rahc/acrylamide.pdf (4 pgs.).

Lindsay Murray, "Acrylamide", found at http://www.inchem.org/documents/pims/chemical/pim652.htm, Jun. 1998 (8 pgs.).

Centre for Molecular and Biomolecular Informatics article entitled "An Amino Acid Bedtime Story", found at http://www.embi.kun.nl.gvteach/HAN/alg/infopages/bedtime.html, material from Friedli Enterprises, Georges-Louis Freidli, PgDip.,MSc.,PhD., Apr. 18, 2002 (3 pgs.).

Home Page for Frostburg State University—Organic Chemistry Help, article entitled "Nucleophilic Addition to Carbonyl Groups" found at http://www.chemhelper.com/nucadd.html, 2000 (1 pg.).

Karl Harrison, article entitled "Amino Acids and Proteins" found at http://www.chem.ox.ac.uk/mom/amino_acids/introduction.html, 1996 (1 pg.).

Karl Harrison, article entitled "Molecules of the Month", found at http://www.chem.ox.ac.uk/mom/, 1996 (1 pg.).

Eur. J. Lipid Sci. Technol. 104 (2002) 762-771 article entitled "Analysis of acrylmide and mechanisms of its formation in deep-fried products" dated Sep. 27, 2002 (10 pgs.).

Nature magazine article entitled "Acrylamide is formed in the Maillard reaction" dated Oct. 3, 2002, which can be found at www.nature.com/nature (1 pg.).

Nature magazine article entitled "Acrylamide from Maillard reaction products" dated Oct. 3, 2002, which can be found at www.nature.com/nature (1 p.).

Deutsche Lebensmittel-Rundschau 98 Jahrgang, Heft article entitled "Formation of Acrylamide in Heated Potato Products—Model Experiments Pointing to Asparagine as Precursor" dated Nov. 2002 (4 pgs.).

C. Benedito De Barber, J.A. Prieto, C. Collar, "Reversed-Phase High-Performance Liquid Chromatography Analysis of Changes in Free Amino Acids During Wheat Bread Dough Fermentation", Cereal Chemistry, Feb. 26, 1989, pp. 283-288, vol. 66, No. 4, American Association of Cereal Chemists, Inc., USA.

Patricia C. Dunlop, Gail M. Meyer, Robert J. Roon, "Nitrogen Catabolite Repression of Asparaginase II in Saccharomyces Cerevisiae", Journal of Bacteriology, Jul. 1980, pp. 422-426, vol. No. 1, Department of Biochemistry, University of Minnesota, Minneapolis, Minnesota 55455.

* cited by examiner

METHOD FOR REDUCING ACRYLAMIDE FORMATION IN THERMALLY PROCESSED FOODS

BACKGROUND OF THE INVENTION

1. Technical Field

The present invention relates to a method for reducing the amount of acrylamide in thermally processed foods. This invention permits the production of foods having significantly reduced levels of acrylamide. The method relies on interfering with an acrylamide formation pathway that begins with the amino acid asparagine.

2. Description of Related Art

The chemical acrylamide has long been used in its polymer form in industrial applications for water treatment, enhanced oil recovery, papermaking, flocculants, thickeners, ore processing and permanent-press fabrics. In very recent times, a wide variety of foods have tested positive for the presence of acrylamide monomer. Acrylamide has especially been found in carbohydrate food products that have been processed at high temperatures. Examples of foods that have tested positive for acrylamide include coffee, cereals, cookies, potato chips, crackers, french-fried potatoes, breads and rolls, and fried breaded meats. Since acrylamide in foods is a recently discovered phenomenon, its mechanism of formation has not been confirmed. But, since the acrylamide monomer is not desired in food products, it would be useful to have a method for its significant reduction or elimination in thermally processed foods.

SUMMARY OF THE INVENTION

This present invention is a method for reducing the amount of acrylamide in thermally processed food products comprising in one embodiment; providing a food ingredient that contains asparagine, subjecting the asparagine-containing food ingredient to asparagine inactivating means, using the asparagine-containing food ingredient as a component in a food mixture, and heating the food mixture to form a thermally processed food. Acrylamide is effectively reduced by reducing the amount of reactive asparagine present in the food or food ingredients prior to thermal processing. In one embodiment, asparagine is contacted with the enzyme asparaginase to convert asparagine to aspartic acid and ammonia. In another embodiment, the ingredients for use in the manufacture of the thermally processed food product are leached to remove asparagine before the food ingredients are heated at temperatures above about 80 C. In yet another embodiment of this invention, the ingredients for use in the manufacture of the food product are fermented to reduce asparagine as microorganisms metabolize asparagine for protein synthesis and other microbial metabolism.

The above, as well as additional features and advantages of the invention will become apparent in the following written detailed description.

DETAILED DESCRIPTION OF THE INVENTION

The formation of acrylamide in thermally processed foods requires a source of carbon and a source of nitrogen. It is hypothesized that carbon is provided by a carbohydrate source and nitrogen is provided by a protein source or amino acid source. Many plant-derived food ingredients such as rice, wheat, corn, barley, soy, potato and oats contain asparagine and are primarily carbohydrates having minor amino acid components. Typically, such food ingredients have a small amino acid pool, which contains other amino acids in addition to asparagine. There are twenty standard amino acids that are the building blocks of proteins and can be found in these food ingredients including, but not limited to, lysine, alanine, asparagine, glutamine, arginine, histidine, glycine and aspartic acid.

By "thermally processed" is meant food or food ingredients wherein components of the food, such as a mixture of food ingredients, are heated at temperatures of at least 80° C. Preferably the thermal processing of the food or food ingredients takes place at temperatures between about 100° C. and 205° C. The food ingredient may be separately processed at elevated temperature prior to the formation of the final food product. An example of a thermally processed food ingredient is potato flakes, which is formed from raw potatoes in a process that exposes the potato to temperatures as high as 200° C. Examples of other thermally processed food ingredients include processed oats, par-boiled and dried rice, cooked soy products, corn masa, roasted coffee beans and roasted cacao beans. Alternatively, raw food ingredients can be used in the preparation of the final food product wherein the production of the final food product includes a thermal heating step. One example of raw material processing wherein the final food product results from a thermal heating step is the manufacture of potato chips from raw potato slices by the step of frying at a temperature of from about 100° C. to about 205° C. or the production of french fries fried at similar temperatures.

In accordance with the present invention, however, a significant formation of acrylamide has been found to occur when the amino acid asparagine is heated in the presence of a simple sugar. Heating other amino acids such as lysine and alanine in the presence of a simple sugar such as glucose does not lead to the formation of acrylamide. But, surprisingly, the presence of asparagine with another amino acid, such as lysine, in the presence of a simple sugar does cause an increase in the formation of acrylamide that is much greater than when asparagine is the only amino acid present.

Having established the rapid formation of acrylamide when asparagine is heated in the presence of a simple sugar, a reduction of acrylamide in thermally processed foods can be achieved by inactivating the asparagine. By "inactivating" is meant removing asparagine from the food or rendering asparagine non-reactive along the acrylamide formation route by means of conversion or binding to another chemical that interferes with the formation of acrylamide from asparagine.

One such method for inactivating is to contact asparagine with the enzyme asparaginase. This enzyme decomposes asparagine to aspartic acid and ammonia. Asparagine may also be inactivated as the precursor of acrylamide in a thermally processed food by leaching. The solubility of asparagine in an aqueous solution will be facilitated when the pH of the solution is maintained as slightly acidic or slightly basic, preferably between a pH of 5 and 9. Asparagine may further be inactivated as the precursor of acrylamide in a thermally processed food by fermentation. Asparagine can also be incorporated into proteins to inactivate asparagine as a precursor to acrylamide. Asparagine may be further inactivated as the precursor of acrylamide by the addition of a divalent cation such as calcium in the form of calcium lactate, calcium citrate or calcium malate. Asparagine may also be inactivated as the precursor of acrylamide by increasing the amount of reducing sugar in the food by the addition of glucose, fructose or rhamnose.

Other techniques will be evident to those skilled in the art to effect the inactivation of asparagine in a way that interferes with the formation of acrylamide. With lower levels of asparagine in the food ingredient or the food product prior to thermal processing, the level of acrylamide in the final processed food will be dramatically reduced.

Several embodiments of the invention are illustrated in the examples set forth below:

EXAMPLE 1

This example demonstrates that acrylamide is not formed in the presence of a simple sugar and the amino acid lysine. About 0.2 grams of glucose was combined with about 0.1 grams of the amino acid L-lysine hydrate and 0.2 mls of water in a 20-ml headspace vial. The vial was covered with aluminum foil and heated in a gas chromatographic oven with the following temperature profile: initial temperature setting of 40° C.; the temperature was then increased 20° C. per minute to 200° C.; there was a two-minute hold at 200° C.; after which the vial was allowed to cool to 40° C. After heating, the mixture had dried out and turned black. The reaction mixture was extracted with one hundred milliliters of water and acrylamide in the water was measured by GC-MS. When glucose was heated with L-lysine hydrate, acrylamide was not detected (detection limit less than 50 parts per billion). If the Maillard reaction was the source of acrylamide, then the lysine reaction mixture should have contained acrylamide because the reaction mixture was extensively browned.

EXAMPLE 2

This example demonstrates that acrylamide is not formed in the presence of a simple sugar and the amino acid alanine. The method of Example 1 was repeated except the amino acid used was L-alanine. Again, acrylamide could not be measured above the detection limit of 50 parts per billion.

EXAMPLE 3

This example demonstrates the formation of acrylamide in the presence of a simple sugar and asparagine. Example 1 was again repeated except that the amino acid was L-asparagine monohydrate. When the reaction mixture was extracted with water and acrylamide measured by GC-MS, the reaction mixture was measured to have 55,106 parts per billion acrylamide. Based on the initial charge of 0.1 gram of asparagine, this represents about a 9% yield of acrylamide.

EXAMPLE 4

This example demonstrates the formation of acrylamide in the presence of a simple sugar, asparagine and a second amino acid. Example 1 was repeated except that equal parts of L-lysine hydrate and L-asparagine monohydrate were each present in an amount of 0.1 grams. The reaction mixture was tested for acrylamide and acrylamide was found at a level of 214,842 parts per billion. Based on the initial charge of asparagine and lysine, this represents about a 37% yield of acrylamide.

EXAMPLE 5

The reduction of acrylamide formation when asparagine and glucose are heated in the presence of the enzyme asparaginase is demonstrated in this example. The enzyme asparaginase was dissolved in 0.05 M tris-hydrocholoric acid buffer at ph 8.6 to make an active asparaginase solution. A control asparaginase solution was also made by heating a portion of the active asparaginase solution at 100° C. for 20 minutes to deactivate the enzyme. In the control, 0.2 grams glucose, 0.1 gram asparagine and 20 mils of the heated asparaginase solution were combined in a 20-ml headspace vial. In the active enzyme experiment, 0.2 grams of glucose, 0.1 grams asparagine and 20 mils of active asparaginase solution were combined in a 20-ml headspace vial. The amount of enzyme in the vial was 250 enzyme units. The control and active enzyme mixtures were processed together in duplicate. The vials were kept at 37° C. for 2 hours, then placed in an 80° C. oven for 40 hours to evaporate to dryness. After heating, 0.2 ml of water was added to each vial. The vials were then heated in a gas chromatographic oven with the following temperature profile: proceeding from an initial temperature of 40° C.; heating 20° C. per minute to 200° C.; and holding at 200° C. for 2 minutes before cooling to 40° C. The reaction mixtures were then extracted with 50 ml water and acrylamide in the water was measure by GC-MS. The values measured are shown in Table 1 below:

TABLE 1

Acrylamide Formation in the Presence of Asparaginase and Glucose

| Test Material | Acrylamide (ppb) | Percent Reduction |
| --- | --- | --- |
| Control 1 | 334,810 | — |
| Control 2 | 324,688 | — |
| Active Asparaginase 1 | 66 | 99.9 |
| Active Asparaginase 2 | 273 | 99.9 |

As can be seen, treatment of the system with an enzyme that decomposes asparagine to aspartic acid and ammonia reduced acrylamide formation by more than 99.9%. This experiment establishes that reducing the concentration of asparagine, or the reactive nature or asparagine, will reduce acrylamide formation.

In addition to inactivating asparagine, plant-derived food ingredients can also be sourced from plants that are bred and selected for having asparagine levels that are lower than those of other similar plants. A reduction in the amount of asparagine in the plant-derived food ingredient will be reflected in the amount of acrylamide that is formed under the same conditions of thermal treatment.

While the invention has been particularly shown and described with reference to one embodiment, it will be understood by those skilled in the art that various other approaches to the inactivation of asparagine may be made without departing from the spirit and scope of this invention.

We claim:

1. A method for the reduction of acrylamide in thermally processed foods comprising the steps of:
    (a) providing a food ingredient that contains free asparagine;
    (b) adding an asparaginase solution to the food ingredient, thereby inactivating asparagine in the asparagine-containing food ingredient;
    (c) using said food ingredient as a component in a food mixture; and
    (d) heating said food mixture to form a thermally processed food.

2. The method of reducing acrylamide formation in thermally processed foods of claim 1 wherein the food ingredient comprises primarily a carbohydrate.

3. The method of reducing acrylamide formation in thermally processed foods of claim 1 wherein the food ingredient is selected from the group comprising rice, wheat, corn, barley, soy, potato and oats.

4. The method of reducing acrylamide formation in thermally processed foods of claim 1 wherein the food ingredient comprises potato.

5. The method of reducing acrylamide formation in thermally processed foods of claim 1 wherein the asparagine-containing food ingredient further comprises at least one other amino acid.

6. The method of reducing acrylamide formation in thermally processed foods of claim 5 wherein the at least one other amino acid is lysine.

7. The method of reducing acrylamide formation in thermally processed foods of claim 1 wherein the inactivating step (b) comprises adding an asparaginase solution to the asparagine-containing food ingredient in the presence of a simple sugar.

8. The method of reducing acrylamide formation in thermally processed foods of claim 7 wherein the simple sugar comprises glucose.

9. The method of reducing acrylamide formation in thermally processed foods of claim 1 wherein the food mixture is heated at step (d) to a temperature of at least 80° C.

10. The method of reducing acrylamide formation in thermally processed foods of claim 1 wherein the thermal processing of the food mixture of step (d) occurs at temperatures between 100° C. and 205° C.

11. A food produced by the method of claim 1.

12. The food of claim 11 wherein said food comprises potato.

13. The food of claim 12 wherein said food comprises potato chips.

* * * * *

UNITED STATES PATENT AND TRADEMARK OFFICE
CERTIFICATE OF CORRECTION

| | |
|---|---|
| PATENT NO. | : 7,037,540 B2 |
| APPLICATION NO. | : 10/247504 |
| DATED | : May 2, 2006 |
| INVENTOR(S) | : Vincent Allen Elder, John Gregory Fulcher and Henry Kin-Hang Leung |

It is certified that error appears in the above-identified patent and that said Letters Patent is hereby corrected as shown below:

In the Specification, column 4: in line 1, change "tris-hydrocholoric" to -- Tris-hydrochloric --; in line 2, change "ph" to -- pH --; in line 39, change "the reactive nature or" to -- the reactive nature of --.

Signed and Sealed this

Twenty-second Day of August, 2006

JON W. DUDAS
*Director of the United States Patent and Trademark Office*